US00PP37013P3

(12) United States Plant Patent
Ioriatti

(10) Patent No.: US PP37,013 P3
(45) Date of Patent: Oct. 14, 2025

(54) ***RUBUS IDAEUS* PLANT NAMED 'BT RASseven'**

(50) Latin Name: *Rubus idaeus*
Varietal Denomination: BT RASseven

(71) Applicant: Diego Ioriatti, Baselga di Pine (IT)

(72) Inventor: Diego Ioriatti, Baselga di Pine (IT)

(73) Assignee: Berrytech SRL (IT)

( * ) Notice: Subject to any disclaimer, the term of this patent is extended or adjusted under 35 U.S.C. 154(b) by 0 days.

(21) Appl. No.: 18/964,279

(22) Filed: Nov. 29, 2024

(65) Prior Publication Data

US 2025/0204293 P1 Jun. 19, 2025

(51) Int. Cl.
*A01H 5/08* (2018.01)
*A01H 5/00* (2018.01)
*A01H 6/74* (2018.01)

(52) U.S. Cl.
USPC ..... Plt./204
CPC ..... *A01H 6/7499* (2018.05); *A01H 5/00* (2013.01); *A01H 5/08* (2013.01)

(58) Field of Classification Search
USPC ..... Plt./204
CPC ..... A01H 5/08; A01H 5/00; A01H 6/7499; A01H 6/74
See application file for complete search history.

(56) References Cited

U.S. PATENT DOCUMENTS

PP22,459 P3 * 1/2012 Maddalena ..... A01H 5/08 Plt./204
PP33,447 P3 * 9/2021 Diego ..... A01H 6/7499 Plt./204

* cited by examiner

*Primary Examiner* — June Hwu

(57) ABSTRACT

A new and distinct cultivar of *Rubus idaeus* plant named 'BT RASseven' is disclosed, characterized by high quality fruits in terms of shelf life. Shelf life is 8 to 9 days at normal fruit cooler temperatures. Plants are semi-erect, including the lateral branches. Fruit has a clear light red color which is maintained during post-harvest. Plants have dense pubescence at the base of the plant. The new cultivar is a *Rubus*, intended for commercial fruit production.

3 Drawing Sheets

Latin name of the genus and species: *Rubus idaeus*.
Cultivar denomination: 'BT RASseven'.

BACKGROUND OF THE INVENTION

The new *Rubus idaeus* cultivar is a product of a planned breeding program conducted by the inventor in Baselgia di Pine, Italy. The objective of the breeding program was to produce new *Rubus idaeus* varieties for commercial applications. The cross resulting in this new cultivar was made during September of 2019.

The seed parent is a proprietary, unpatented cultivar referred to as *Rubus* 'BT17AC190'. The pollen parent is the unpatented proprietary cultivar *Rubus* 'BPDRE'. The new cultivar was selected during the August of 2021 by the inventor in a group of seedlings resulting from the 2019 crossing, in a research greenhouse in Baselgia di Pine, Italy.

The inventor has filed an application with the CPVO Dec. 13, 2023, having application number 2023/2724. This disclosure falls within the exception allowed under 102(b)(1).

Asexual reproduction of the new cultivar was performed by vegetative suckers. This was first performed at a research greenhouse in Baselgia di Pine, Italy during February of 2022 and has shown that the unique features of this cultivar are stable and reproduced true to type in multiple successive generations.

SUMMARY OF THE INVENTION

The cultivar 'BT RASseven' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BT RASseven'. These characteristics in combination distinguish 'BT RASseven' as a new and distinct *Rubus* cultivar:

1. High quality of the fruits in terms of shelf life. Shelf life is 8 to 9 days at a normal fruit cooler temperature (approximately 1° C. to 4° C.).
2. Clear light red color of the fruits.
3. Semi-upright architecture of the canes and lateral branches.
4. Good tolerance to certain raspberry pests and diseases. Observed good tolerance for raspberry aphid, *Amphorophora idaei* and leafhoppers, *Edwardsiana rosae*. Good tolerance to common strains of raspberry orange rust.
5. Dense pubescence at the base of the plant.

PARENT COMPARISON

Plants of the new cultivar 'BT RASseven' are similar to plants of the seed parent, in most horticultural characteristics, however, plants of the new cultivar 'BT RASseven' differ in the following:

1. The new cultivar produces fruit which are more homogenous in size.
2. The new cultivar has a lighter fruit color.
3. The new cultivar has less spinescence.

4. The new cultivar produces shorter fruit laterals and a more erect architecture.
5. Budbreak occurs on the floricane of the new cultivar more regularly than the seed parent cultivar.

Plants of the new cultivar 'BT RASseven' are similar to plants of the pollen parent, in most horticultural characteristics, however, plants of the new cultivar 'BT RASseven' differ in the following:

1. The new cultivar produces taller primocane.
2. The new cultivar has lower remontancy.
3. The new cultivar fruits later on primocane.
4. The new cultivar produces less branches than the pollen parent cultivar.
5. The new cultivar produces fruit which is more conical in shape than fruit of the pollen parent.

COMMERCIAL COMPARISON

Plants of the new cultivar 'BT RASseven' are comparable to the cultivar *Rubus* 'BT RASTWO', U.S. Plant Pat. No. 33,447. The two *Rubus* varieties are similar in most horticultural characteristics, however, the new cultivar 'BT RASseven' differs in the following:

1. The new cultivar produces more branches.
2. The new cultivar has a lower chill requirement; about 500 hours compared to 600 hours.
3. The new cultivar has a later primocane fruit harvest.
4. The new cultivar produces firmer fruit with a better shelf life. Shelf life of the new cultivar is 2 to 3 days longer in a commercial cooler.
5. The new cultivar has thinner leaves.

Plants of the new cultivar 'BT RASseven' can also be compared to the commercial cultivar *Rubus* 'BP1' U.S. Plant Pat. No. 22,459. These varieties are similar in most horticultural characteristics however, the new cultivar 'BT RASseven' differs in the following:

1. The new cultivar is more productive both on primocane and on floricane harvest.
2. The new cultivar produces less spinescence.
3. The new cultivar has a more upright architecture.
4. The new cultivar produces fruit with a lighter and more stable color in postharvest.
5. The new cultivar produces few to medium primocanes from the ground; this comparator produces medium to many.

BRIEF DESCRIPTION OF THE PHOTOGRAPHS

The photographs were taken using conventional techniques and although colors may appear different from actual colors due to light reflectance it is as accurate as possible by conventional photographic techniques. Colors in the photographs may appear to differ slightly from the color values cited in the botanical description, which accurately describe the colors.

DETAILED BOTANICAL DESCRIPTION

Figure 1:
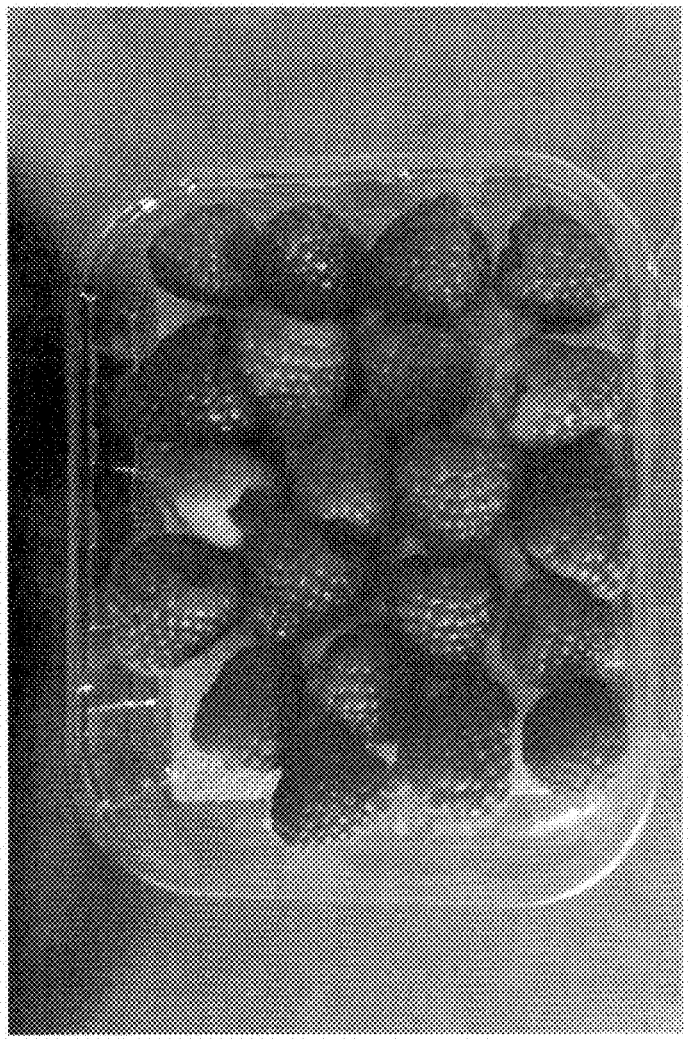
FIG. 1 illustrates in full color harvested fruit of 'BT RASseven'.
Figure 2:
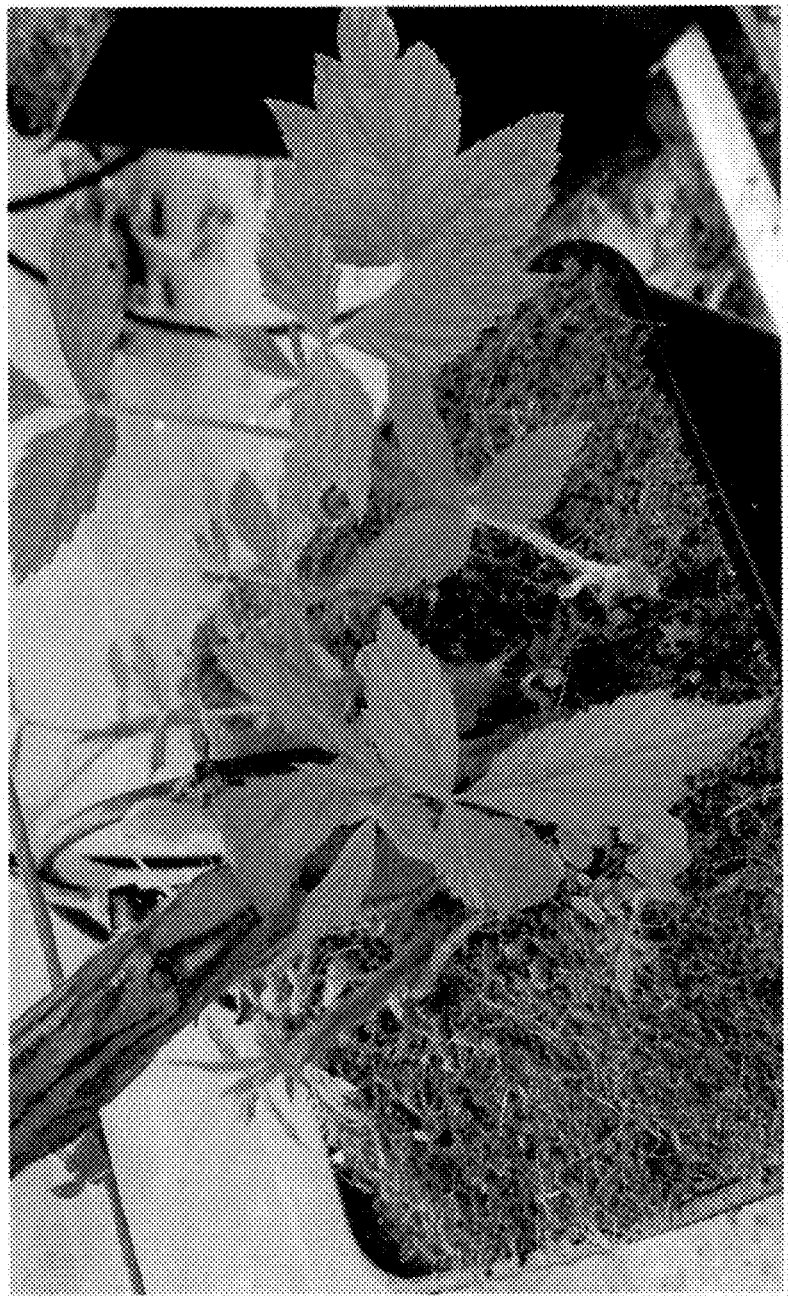
FIG. 2 illustrates in full color the base of a plant of 'BT RASseven', with typically dense pubescence.
Figure 3:
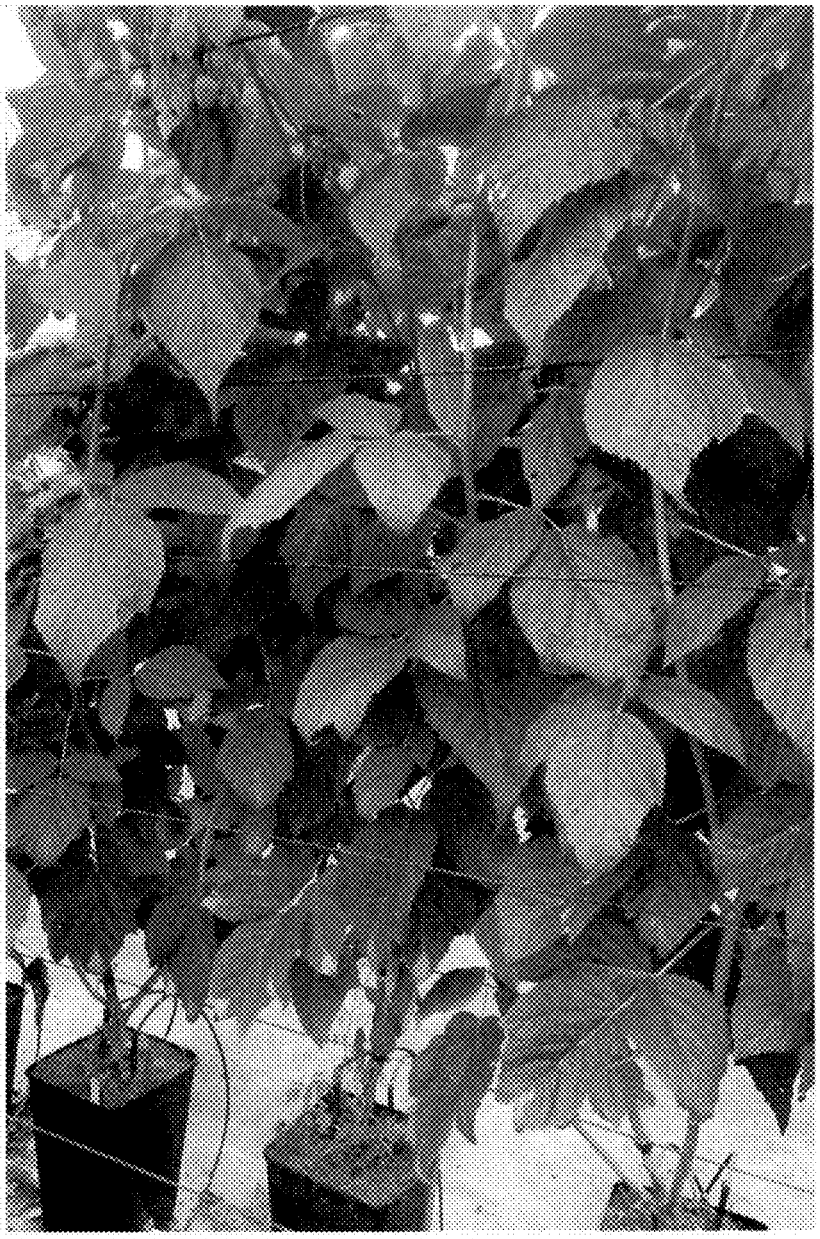
FIG. 3 illustrates in full color typical plants of 'BT RASseven'. Age of the plants is approximately 1 year old grown in a poly hoop house.

In the following description, color references are made to The Royal Horticultural Society Colour Chart 2007 except where general terms of ordinary dictionary significance are used. The following observations and measurements describe 'BT RASseven' plants which were grown in Borgo Valsugana, Trento, Italy. Plants were grown in a season tunnel, given approximately 30% shading during Summer. The growing temperature ranged from about 15° C. to 34° C. during the day and from about 8° C. to 22° C. during the night. Measurements and numerical values represent averages of typical plant types. Plants are approximately 1 year old.

Botanical classification: *Rubus idaeus* 'BT RASseven'.

PROPAGATION

Time to initiate roots: About 35 days at approximately 16° C.

Time to produce a rooted cutting: About 45 days at 18° C.

PLANT

Age of plant described: About 1 year.
Plant spread: Approximately 70 cm.
Plant height: Approximately 200 cm.
Habit: Semi-upright.
Floral bud burst: Mid-April.
Cane emergence: Mid-May.
Primocane length: Approx. 230 cm.
Primocane color: Near RHS Yellow-Green 151B.
Anthocyanin coloration present: Not typical.
Young shoot anthocyanin coloration at apex: Weak.
Dormant cane color: Near RHS Greyed-Orange 164A.
Primocane diameter: Average 1.2 cm.
Primocane quantity: Few to medium.
Floricane length: Long. 25 to 45 cm.
Floricane attitude of fruiting laterals: Semi-upright.
Internode length: Average 5 cm.
Spines:
*Approximately density/quantity of spines*.—Extremely high density of small spines at the base level. About 30 to 40 cm of height, moderate density of spines, approximately 3 to 4 per cm of stem length at 1 meter of height.
*Length*.—Average range 2 to 3 mm.
*Color*.—Near RHS Brown 200A.
*Shape*.—Short deltate.

FOLIAGE

Leaf: Average of lateral and terminal leaflets.
*Arrangement*.—Compound opposite.
*Quantity*.—9-10 per stem.
*Average length*.—Approximately 26 cm.
*Average width*.—Approximately 18 to 20 cm.
Leaflet:
*Quantity*.—Most common quantity of leaflets per leaf: 3.
*Average length*.—Approximately 14-19 cm.
*Average width*.—Approximately 7-10 cm.
*Shape of blade*.—Overall broad deltate.
*Apex*.—Acuminate.
*Base*.—Broad rounded.
*Margin*.—Double serrate.
*Texture of top surface*.—Coriaceous.
*Texture of bottom surface*.—Coriaceous.
*Pubescence*.—Low.
*Leaf internode length*.—6-9 cm.

*Color*.—Young foliage upper side: Near RHS Yellow-Green 144B. Young foliage under side: Near RHS Green 142B. Mature foliage upper side: Near RHS Green 141B. Mature foliage under side: Near RHS Green 134B.

*Venation*.—Type: Cross veniculate, pinnate along main axis. Venation color upper side: Near Yellow-Green 144C. Venation color under side: Near Yellow-Green 144D.

*Petiole*.—Length: 6 to 8 cm. Width: 3 mm. Color: Near RHS Yellow-Green N144C. Texture: Glabrous.

*Rachis*.—Length: 12-13 cm. Width: 3-4 mm. Color: Near RHS Yellow-Green N144C. Texture: Glabrous.

*Stipules*.—Not observed.

FLOWER

Floral bud burst date: Approximately July 25 for primocane flowers in Northern Italy.

Floricane florane bud burst date: Around May 25 in Northern Italy.

Flowering season: Begins around August 20 in Verona, Italy.

Inflorescence:

*Flowers per*.—15-24.

Flower size:

*Diameter*.—Approximately 2 cm.

*Length*.—Approximately 1 cm.

Peduncle:

*Length*.—5 cm.

*Diameter*.—0.2 cm.

*Color*.—Near RHS Yellow-Green N144C.

*Anthocyanin intensity*.—Weak.

*Texture*.—Glabrous.

Pedicel:

*Length*.—1.3 cm.

*Diameter*.—2 mm.

*Color*.—Near RHS Yellow-Green N144C.

*Texture*.—Glabrous.

Petals:

*Petal arrangement*.—Rotate.

*Length*.—9 mm.

*Width*.—5 mm.

*Shape*.—Semi-cuneate.

*Margin*.—Entire.

*Apex*.—Rounded.

*Base*.—Rounded.

*Petal quantity*.—5.

*Texture*.—Glabrous.

Color: Petals:

*When opening*.—Upper surface: Near RHS White N155B. Lower surface: Near RHS White N155B.

*Fully opened*.—Upper surface: Near RHS White N155B. Lower surface: Near RHS White N155B.

Bud:

*Shape*.—Ovate.

*Length*.—Approximately 6 mm.

*Diameter*.—Approximately 4 mm.

*Color*.—Near RHS Greyed-Orange 166B.

*Sepals*.—

*Length*.—1.5 cm.

*Width*.—6 mm.

*Shape*.—Narrow deltate with apiculate apex.

*Color*.—Interior Surface: Near RHS Green 140C. Exterior Surface: Near RHS Green 141B.

*Texture*.—Glabrous.

REPRODUCTIVE ORGANS

Androecium:

*Stamens*.—

*Number*.—120 to 135.

*Filament length*.—Approximately 6 mm.

*Filament color*.—Near RHS Green-White 157A.

Anthers:

*Length*.—0.8 mm.

*Shape*.—Ovate.

*Color*.—Near RHS Greyed-Orange 164A.

*Pollen*.—Quantity: Moderate. Color: Near RHS White N155C.

Pistil:

*Number*.—135 to 145.

*Length*.—Approximately 4 mm.

*Style*.—Length: Approximately 4 mm. Color: Near RHS Green-White 157A.

FRUIT

Market use: Fresh consumption.

Length: 4.5 to 5 cm.

Diameter: 2.7 to 3 cm.

General shape in lateral view: Round-conical.

Color: Near RHS Red 43B, 43C and 43D.

Average druplets per berry: 180.

Average weight per berry: 5.5 to 6 grams.

Brix: 9.6 on primocane fruit harvested in July.

Firmness: Medium.

Fruit bearing on floricane/primocane or both: Both. Fruit produced on floricane and primocane are identical.

Fruit begins ripening: Primocane about August 25th; floricane about April 15$^{th}$.

Fruiting season: Primocane September 15 to November; floricane June to mid-July.

Yield per hectare: 15 to 19 ton/ha in primocane; 23 to 24 ton/ha in floricane.

Other fruit characteristics: Clear colored fruit of medium size with very slow darkening compared to most commercial varieties. Very stable clear color also maintained after harvest.

OTHER CHARACTERISTICS

Disease/pest resistance/susceptibility: Observed good tolerance for raspberry aphid, *Amphorophora idaei* and leafhoppers, *Edwardsiana rosae*. Good tolerance to common strains of raspberry orange rust. Some susceptibility to powdery mildew has been observed especially on young shoots.

Temperature tolerance: Maximum 36° C. during pollination and harvest. Good tolerance to winter frosts to −15° C.

What is claimed is:

1. A new and distinct cultivar of *Rubus idaeus* plant named 'BT RASseven' as herein illustrated and described.

* * * * *